United States Patent [19]

Ochi

[11] Patent Number: 4,914,085
[45] Date of Patent: Apr. 3, 1990

[54] ANTIRHEUMATIC AGENT

[75] Inventor: Takahiro Ochi, Kawanishi, Japan

[73] Assignee: Otsuka Pharmaceutical Co., Ltd., Tokyo, Japan

[21] Appl. No.: 51,598

[22] Filed: May 20, 1987

[30] Foreign Application Priority Data

May 21, 1986 [JP]　Japan ................. 61-116703

[51] Int. Cl.$^4$ .................. A61K 31/70; A61K 31/715; A61K 37/20
[52] U.S. Cl. ..................................... 514/25; 514/825; 514/54; 424/450; 536/1.1; 536/18.7
[58] Field of Search ........................ 514/825, 25, 54; 424/450; 536/1.1, 18.7

[56] References Cited

PUBLICATIONS

"The Journal of Biological Chemistry", vol. 259, No. 7, pp. 4672 to 4680 (1980).

Primary Examiner—Ronald W. Griffin
Attorney, Agent, or Firm—Finnegan, Henderson, Farabow, Garrett & Dunner

[57] ABSTRACT

Antirheumatic agent containing, as the active ingredient, a specific glycolipid such as difucosyl neolactonoroctasosylceramide or trifucosyl neolactonoroctaosylceramide. Said glycolipids are known compounds which are isolated from human adenocarcinoma. However, up to the date, there have not been known that these glycolipids possess any pharamcological activities relating to the rheumatoid arthritis.

Said antirheumatic agent may preferably be used as injectable pharmaceutical preparations.

3 Claims, No Drawings

ANTIRHEUMATIC AGENT

FIELD OF THE INVENTION

The present invention relates to an antirheumatic agent, more particularly, it relates to a novel antirheumatic agent containing, as the active ingredient, the specific glycolipid.

PRIOR ART

Rheumatoid arthritis (RA) is a systemic disease which is accompanied with the specific inflammations of the joints, and such inflammations develop multitudinously result syndromes related thereto. Such syndromes usually progress to chronic disease due to the repetitions of remission and recrudescent, and in the most cases rheumatoid arthritis results the destruction and deformity of the joints. [Cf. "RINSHŌ-TO-KENKYŪ" (Clinic and Research), Vol. 54, No. 10, pages 7 (3143) to 13 (3149), October, 1977.]

The causes of rheumatoid arthritis have not been understood as yet, and the substantial methods for treating and curing of rheumatoid arthritis have not been established yet, at the present stage, some nosotropic pharmacotherapies are only applied as to the major medical treatments. [Cf. "NAIKA-MOOK" (Internal Medicine Mazine-book), No. 13, a special article entitled "Chronical Rheumatoid Arthritis of the Joints", pages 123–130, (1980); "RINSHO-TO-KENKYU" (Clinic and Research), Vol. 54, No. 10, pages 14 (3150) to 19 (3155), October, 1977.]

Under the circumstances, novel pharmaceutical preparations which can be able to possess remarkable effects for treating and curing rheumatoid arthritis have keenly been desired.

SUMMARY OF THE INVENTION

It is an object of the present invention to provide novel antirheumatic agent which can be able to make causal treatment and cure of rheumatoid arthritis.

Another object of the present invention is to provide a method for treating and curing rheumatoid arthritis.

DETAILED DESCRIPTION OF PREFERRED EMBODIMENTS

The above-mentioned objects of the present invention can be achieved by administering antirheumatic drugs containing, as the active ingredient, a glycolipid represented by the general formula (1),

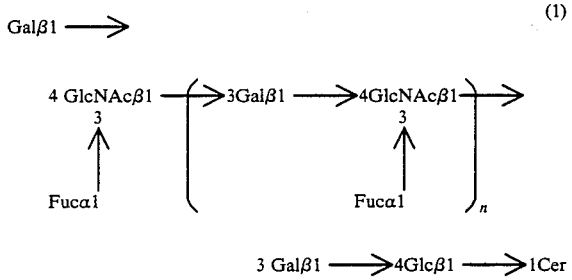

(wherein n is 1 or 2).

In the present specification, the abbreviations used for explaining the glycolipid represented by the general formula (1) and other substances are indicated by nomenclature and symbols provided by International Pure and Applied Chemistry (IUPAC) and International Union of Biology (IUB). The examples of these abbreviations are as follows:
Gal: galactose
Fuc: fucose
Glc: glucose
Cer: ceramide
GlcNAc: N-acetylglucosamine.

The present inventors have made extensive studies on the nosogenesis and pathogenic physiology of rheumatoid arthritis, especially studied the relativity of immunological abnormality to rheumatoid arthritis. As to the results of the studies, the present inventors have found the facts that the specific glycolipids represented by the general formula (1) possess surprisingly pharmacological activities for fulfilling the above-mentioned objects of the present invention.

Such pharmacological activities of the glucolipids are quite effective for treating of rheumatoid arthritis in clinical use, thus the present invention was established on the basis of said findings.

The glycolipids represented by the general formula (1), thus difucosyl neolactonorhexaosylceramide (i.e., n in the general formula (1) is 1); and trifucosyl neolactonoroctaosylceramide (i.e., n in the general formula (1) is 2) are known compounds which have been isolated from human adenocarcinoma. [Cf. "The Journal of Biological Chemistry", Vol. 259, No. 7, pages 4672 to 4680, (1980).]

The specific chemical structures of these glycolipids have been considered as the specific antigenic structures against human cancers. However, any academic paper has not reported relating to pharmacological activity of these glycolipids as yet. Furthermore, there have never been known whether these glycolipids have any activity relating to rheumatoid arthritis.

The glycolipids represented by the general formula (1), any one of which is contained as the active ingredient in the antirheumatic agent of the present invention, are known in the above-mentioned prior art literature, thus these glucolipids can be prepared by methods as disclosed in said prior art literature.

Furthermore, the monoclonal antibodies which can be able to recognize the sugar structures of these glycolipids have already been reported, and thus in case of preparing these glycolipids, such antibodies can be used. [Cf. "The Journal of Biological Chemistry", Vol. 259, No. 7, pages 4681 to 4685, (1980).]

The pharmaceutical composition according to the present invention containing, as the active ingredient, the above-mentioned glycolipid is prepared by formulating with suitable pharmaceutically acceptable carriers so as to obtain the desired pharmaceutical compositions. Examples of such pharmaceutically acceptable carriers are selected depending on the desired form of pharmaceutical compositions including diluents and excipients such as fillers, diluents, binders, wetting agents, disintegrating agents, surface active agents and others. Pharmaceutical compositions can be selected from any desired administration unit form, and there is not any specific restriction. Generally, in the rheumatic agent according to the present invention, injection preparations, such as solutions, suspensions and emulsions are preferable.

Pharmaceutical compositions can be prepared in dried form product which can be used as a liquid state by adding a suitable liquid carrier before use. If necessary, any additives such as dissolving auxiliaries, buffering agents, analgesic agents, preservitives, coloring agents and others can also be added to the desired pharmaceutical preparations. In addition to the above, liposome form of pharmaceutical compositions is specifically preferable for the antirheumatic agent according to the present invention.

The antirheumatic agent according to the present invention can be administered in various forms of pharmaceutical preparations without any restriction. For example, injection preparations of the antirheumatic agent can be administered intravenously singly or in combination with usual injectable transfusions such as Linger's solution, glucose solution and others. If necessary, the injection preparations are administered singly intramuscularly, intracutaneously, subcutaneously or intraperitoneally.

The amount of the active ingredient to be contained in the antirheumatic agent according to the present invention is not specifically restricted, it can suitably be selected from a wide range depend on method for administrations, mode of administration, the purpose of use, the condition of the patient and the degree of the symptoms. Generally, the active ingredient is administered in an amount of from 50 to 1,000 ng per day an adult patient, and the content of the active ingredient in the antirheumatic agent can be selected suitably depend on the dosage of the active ingredient to be administered to the patient.

EFFECTS OF THE INVENTION

Antirheumatic agent according to the present invention is quite useful agent for preventing and treating rheumatoid arthritis. Thus, by administering said antirheumatic agent, there can be observed decreasing and/or negativing of the rheumatoid factor (RF). Furthermore, there are confirmed normalizing of various inflammatory markers, such as erythrocytes sedimentation reaction value (ESR), C-reactive protein value (CRP) and others. As the results of normalizing of these inflammatory markers, pains caused by arthritis are improved, so that it is possible to reduce the dosage of or break off of anti-inflammatory agents and analgesic agents. In addition to the above-mentioned effects, activity for inhibiting the development of diaclasis or fracture of the bones are also appeared and can be expected. Yet further, by administering the antirheumatic agent of the present invention, preferably effects for improving the systemic syndromes such as easy-feeling of fatigue and also effects for improving activities in daily life of the patient are observed. As explained above, the antirheumatic agent according to the present invention is clinically quite effective agent for preventing and treating rheumatoid arthritis.

The present invention will be explained more in detail by referring to Examples for the purpose of clarifying antirheumatic agent according to the present invention and clinical effects thereof. However, the present invention will not be restricted only to those Examples.

EXAMPLE 1

Pharmaceutical Preparation of the Present Invention

A pharmaceutical preparation in the form of liposomes was prepared by a method according to an article written by Batzri and Korn: Biochimica et Biophysica Acta, 298, (1973), pp. 1015–1019, under sterilized conditions.

200 Micrograms of difucosyl neolactonorhexaosylceramide (hereinafter referred to as "F-2"), a solution being prepared by dissolving 8.5 mg of lecithin in 1 ml of ethanol, and a solution being prepared by dissolving 5 mg of cholesterol in 1 ml of ethanol were admixed, then the resulting mixture was poured vigorously into 20 ml of phosphate buffered saline (PBS) being warmed at about 50° C., by using a vortex-mixer. The resulting mixture was dialyzed in a physiological sodium chloride solution overnight, then filtered (by using a membrane filter of 5 micrometers). 0.2 Milliliter each of the filtrate was filled in a vial to prepare an antirheumatic agent containing 500 nanograms of the active ingredient (F-2) per each vial.

EXAMPLE 2

Clinical Test Results

Clinical tests were conducted in the following 8 patients of rheumatoid arthritis (average age: 53.6 years old, and average morbidity period: 6.7 years) rated as heavier than "definite" stage.

0.2 Milliliter of antirheumatic agent of the present invention (prepared in Example 1, containing 500 nanograms of F-2 as the active ingredient per 1 vial) was administered (counted as one shot) by subcutaneous injection to the forearm of each of the patients. Continuous administrations for 2 days were conducted as one unit of course of treatment (one Kur). One unit of the course of treatment was conducted in every 2 weeks, and said unit of the course of treatment was repeated 7 to 9 times. About 4 months after the beginning of the administration, the patients were clinically examined and evaluated. The test results obtained are shown as follows.

(1) Case-1: Female, age 53; morbidity period 8 years.
  Rated as definite stage of RA, Class II.
  Painful swellings were observed in a number of joints in both hands, both legs and both elbows, and suffered from pains. Marked erosive changes were also observed in the joints by X-ray examination.

|  | ESR(mm/hr) | CRP(mg/dl) | RF(IU/ml) |
|---|---|---|---|
| (1) At the beginning of administration of F-2: | 65 | 2.4 | 23 |
| (2) After 5 units of the course of treatments were finished: (a) | 35 | 1.4 | 0 |
| (3) After 8 units of the course of treatments were finished: (b) | 21 | 0.7 | 0 |

Note:
(a) Along with decreasing of the arthritis symptoms, administration amounts of anti-inflammatory analgesic suppository used habitually were reduced, and considerably improvements of RA were clearly observed.
(b) Remission of active inflammations were observed.

(2) Case-2: Female, age 46, morbidity period 1.5 years.
  Rated as definite stage of RA, Class II.
  At the first medical examination, swellings were observed in hands, fingers and toes, also complained pains and morning stiffness. In daily life activities, mainly the functions of hands were disturbed. Destructions caused by rheumatoid arthritis, erosive changes in the joints were observed by X-ray examination.

|  | ESR(mm/hr) | CRP(mg/dl) | RF(IU/ml) |
|---|---|---|---|
| (1) At the begin- | 32 | 1.0 | 0 |

|  | ESR(mm/hr) | CRP(mg/dl) | RF(IU/ml) |
|---|---|---|---|
| ning of administration of F-2: | | | |
| (2) After 3 units of the course of treatments were finished: (c) | 8 | 0 | 0 |

Note:
(c) Arthritis symptoms were disappeared and complete remission was observed.

One year after the treatments, neither recrudescent nor recurrence of RA were occurred, and the patient did not complain any stiffness of the fingers, and is now enjoying play golf and other sports. This case is considered as an excellent example of the effects shown by antirheumatic agent of the present invention.

(3) Case-3: Female, age 66, morbidity period 5 years.
Rated as Classic stage of RA, Class III.

Medical examination was conducted with the complains flexion contractures of both knees with pains as well as abasia, and stiff contruction of fingers of hands with pains of right hand joints. Conservative therapy was made on both knees by stretching, and fixation of right hands joints was also made.

|  | ESR(mm/hr) | CRP(mm/dl) | RF(IU/ml) |
|---|---|---|---|
| (1) At the beginning of administration of F-2: | 126 | 2.5 | 35 |
| (2) After 4 units of the course of treatments were finished: (d) | 11 | 0 | — |

Note:
(d) In consequence with the reduction of inflammatory symptoms, improvements of systemic syndromes caused by RA were observed. Also observed improvements clearly in daily life activities, such that the patient can be able to use a spoon and others.

(4) Case-4: Female, age 54, morbidity period 8 years.
Rated as definite stage of RA, Class II.

Edemas in a numbers of joints of both knees, both shoulders, both elbows as well as both hands were observed. The patient complained pains with functional disturbances in her daily life activities. Erosive destructions of many joints were observed by X-ray examination. The patient was treated with gold therapy (gold sodium thiosulfate and thiomalate) for about 4 years, but not any effects was observed.

|  | ESR(mm/hr) | CRP(mg/dl) | RF(IU/ml) |
|---|---|---|---|
| (1) At the beginning of administration of F-2: (e) | 110 | 3.2 | 91 |
| (2) After 7 units of the course of treatments were finished: (f) | 31 | 0 | — |

Note:
(e) Complained morning stiffness for over 4 hours every day.
(f) There were observed clear improvements in the arthritis inflammatory syndromes, such as lower of pains in the joints, disappearing of morning stiffness and others.

(5) Case-5: Female, age 54, morbidity period 8 years.
Rated as definite stage of RA, Class II.

Edemas in the joints of both hands, fingers, toes and both elbows. The patient complained pains as well as functional disturbances. Erosions in the joints were observed by X-ray examination.

|  | ESR(mm/hr) | CRP(mg/dl) | RF(IU/ml) |
|---|---|---|---|
| (1) At the beginning of administration of F-2: | 100 | 0.6 | 65 |
| (2) After 9 units of the course of treatments were finished: (g) | 91 | 0.7 | |

Note:
(g) Not any remarkable changes in the rheumatic markers were observed, but observed negativing of RF (continuously) in consequence of the reduction of arthritis syndromes.

(6) Case-6: Female, age 51, morbidity period 10 years.
Rated as definite stage of RA, Class II.

The patient complained edemas in the joints of hands, fingers of the hands, and feet, with pains.

|  | ESR(mm/hr) | CRP(mg/dl) | RF(IU/ml) |
|---|---|---|---|
| (1) At the beginning of administration of F-2: | 112 | 2.7 | 0 |
| (2) After 8 units of the course of treatments were finished: (h) | 42 | 0 | — |

Note:
(h) In consequence of the normalizing ESR and RF levels, the pains in the joints were reduced, and the activities in daily life, such as going down the stairs and others were improved.

(7) Case-7: Female, age 56, morbidity period 10 years.
Rated as definite stage of RA, Class II.

Edemas in a numbers of joints of both shoulders, both hands, fingers of both hands, both knees and both feet were observed, and the patient complained pains. Erosive destructions in the joints were observed by X-ray examination.

|  | ESR(mm/hr) | CRP(mg/dl) | RF(IU/ml) |
|---|---|---|---|
| (1) At the beginning of administration of F-2: | 63 | 2.6 | 117 |
| (2) After 7 units of the course of treatments were finished: (i) | 16 | 2.6 | 79 |

Note:
(i) In the consequence of the improvements of inflammatory symptoms in the joints and the systemic syndromes, the activities in daily life, such as going down the stairs and others were clearly improved.

(8) Case-8: Male, age 49, morbidity period 3 years.
Rated as definite stage of RA, Class II.

Edemas in the joints of both hands, fingers of hands, and feets were observed, and the patient complained that daily life activities by hands and feet were disturbed. Erosive destructions were observed by X-ray examination and painful swellings were also observed in a numbers of joints.

|  | ESR(mm/hr) | CRP(mg/dl) | RF(IU/ml) |
|---|---|---|---|
| (1) At the beginning of administration of F-2: | 24 | 2.4 | 226 |
| (2) After 7 units of the course of treatments were | 2 | 0 | 155 |

|   | ESR(mm/hr) | CRP(mg/dl) | RF(IU/ml) |
|---|---|---|---|
| finished: (j) | | | 5 |

Note:
(j) In consequence of the remission of active inflammations and break off of the use of anti-inframmatory analgesic supposities, there were observed significant improvements in the activities of daily life.

What is claimed is:

1. A method for treating rheumatoid arthritis characterized by administering a glycolipid represented by the general formula (1),

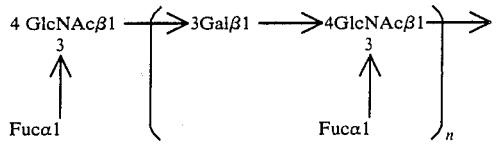

(wherein n is 1 or 2).

2. The method according to claim 1, wherein the glycolipid represented by the general formula (1) is difucosyl neolactonorhexaosylceramide (wherein n is 1).

3. The method according to claim 1, wherein the glycolipid represented by the general formula (1) is trifucosyl neolactonoroctaosylceramide (wherein n is 2).

* * * * *